United States Patent [19]

Sasaki et al.

[11] Patent Number: 4,769,475

[45] Date of Patent: Sep. 6, 1988

[54] BIS(HYDROXYPHTHALIMIDE) AND PROCESS FOR PREPARING THE SAME, AND PROCESS FOR PREPARING POLYESTERIMIDE BY THE USE THEREOF

[75] Inventors: Shigekuni Sasaki, Iruma; Yoshinori Hasuda, Tokyo, both of Japan

[73] Assignee: Nippon Telegraph and Telephone Corporation, Tokyo, Japan

[21] Appl. No.: 839,685

[22] Filed: Mar. 14, 1986

[30] Foreign Application Priority Data

Mar. 19, 1985 [JP] Japan ................................. 60-55151
Oct. 25, 1985 [JP] Japan ............................... 60-238649

[51] Int. Cl.$^4$ ............................................ C07D 209/48
[52] U.S. Cl. ..................................... 548/462; 528/318
[58] Field of Search ........................................ 548/462

[56] References Cited

U.S. PATENT DOCUMENTS 3,920,697 11/1975 Takekoshi et al. .................. 548/462
4,535,170 8/1985 Sonnenberg .......................... 548/462
4,550,208 10/1985 Disteldorf et al. ................... 548/462

FOREIGN PATENT DOCUMENTS 1951632 5/1971 Fed. Rep. of Germany ...... 548/462

OTHER PUBLICATIONS

B. Mandal et al, J. Polym. Sci., Polym. Lett. Ed., vol. 23, 317-322 (1985). Polyetherimide from Dihydroxybisimide.

*Primary Examiner*—Mary E. Ceperley
*Attorney, Agent, or Firm*—Frishauf, Holtz, Goodman & Woodward

[57] ABSTRACT

The present invention provides a bis(hydroxyphthalimide) prepared by reacting 4-hydroxyphthalic anhydride and an organic diamine in the presence of an organic solvent under heating. The bis(hydroxyphthalimide) has two intramolecular imide rings and active hydrogens, and is thus polymerizable to form a variety of polycondensation products each having imide rings by condensation. The bis(hydroxyphthalimide) is also reacted with a dicarboxylic acid dihalide to form a polyesterimide, through condensation, which is excellent in transparency and heat resisting property.

4 Claims, 1 Drawing Sheet

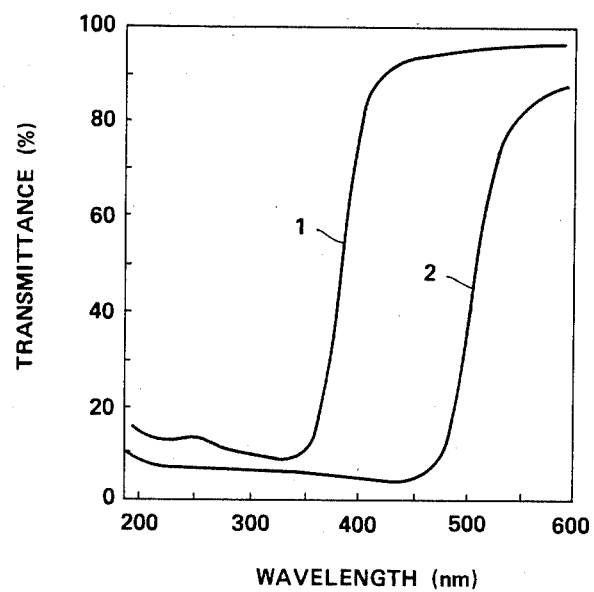

BIS(HYDROXYPHTHALIMIDE) AND PROCESS FOR PREPARING THE SAME, AND PROCESS FOR PREPARING POLYESTERIMIDE BY THE USE THEREOF

BACKGROUND OF THE INVENTION

1. Field of the Invention

This invention relates to a novel bis(hydroxyphthalimide) and a process for preparing the same, and also relates to a process for preparing a polyesterimide using the aforementioned bis(hydroxyphthalimide).

2. Related Art Statement

It has been known in the art that a compound having therein an imide ring has excellent heat resisting property, and that a polyimide is particularly superior in heat resisting property amongst the known heat resisting polymers. The polyimide resins having such advantageous properties have been widely used in the arts of aerospace and aeroplane engineerings, and also in general industrial fields for the production of printed circuit boards, package materials, varnishes for coating electric wires, etc. By the incorporation of an imide ring in a certain polymer, the heat resistant property of the polymer is improved by the advantageous influence afforded by the introduced imide ring. For example, there is a report describing that the heat resistant property of an epoxy resin has been improved by the introduction of an imide ring so that the maximum durable temperature of the modified resin is raised by about 100° C. The polymers having intramolecular imide rings, including polyimides, are expected for further development in view of their excellent heat resistant properties. However, the known polyimides have a disadvantage that they are inferior in percent transmission to visible light rays. Another barrier arresting the development of polyimide resins is that the monomer which may be used as a starting material for a variety of imide ring-containing polymers, as comparable to bisphenol A used for preparing various polymers, is not yet known, although various polyimides or imide ring-containing polymers have been synthesized and used.

After eager pursuit to find an imide ring-containing monomer which may be used as a starting material for the preparation of various imide ring-containing polymers, we have found that a novel bis(hydroxyphthalimide) which is adapted for use as a starting material for various imide ring-containing resins. The bis(hydroxyphthalimide) provided by the invention affords a further merit that a polyesterimide excellent both in transparency and heat resistant property is produced therefrom.

The novel bis(hydroxyphthalimide) provided by the present invention is represented by the following general formula of:

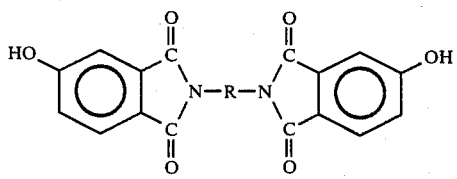

wherein R is a difunctional organic group selected from the group (a), (b) and (c) of:

(a) aromatic hydrocarbon groups having 6 to 20 carbon atoms or a halogenated derivatives thereof;
(b) alkylene groups: and
(c) those represented by the following general formula of:

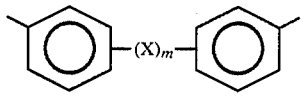

wherein X is a group selected from the group consisting of —O—,

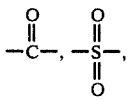

—S—, —C$_n$H$_{2n}$—; m is an integer of 1 or zero; and n is an integer of 1 to 5.

The novel bis(hydroxyphthalimide) set forth above may be prepared by reacting 4-hydroxyphthalic anhydride with an organic diamine represented by the following general formula in the presence of an organic solvent:

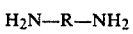

H$_2$N—R—NH$_2$ wherein R is the same as defined above.

Examples of organic diamine which may be conveniently used in the preparation of the bis(hydroxyphthalimide) in the present invention include m-phenylenediamine, p-phenylenediamine, 4,4′-diaminodiphenylpropane, 4,4′-diaminodiphenylmethane, benzidine, 4,4′-diaminodiphenylsulfide, 4,4′-diaminodiphenylsulfone, 4,4′-diaminodiphenyl ether, 1,5-diaminonaphthalene, 3,3′-diaminobenzidine, 3,3′-dimethoxybenzidine, 2,4-bis( -amino-t-butyl)toluene, bis(p- -amino-t-butylphenyl)ether, bis(p- -methyl-o-aminobenzyl)benzene, 1,3-diamino-4-isopropyl benzene, 1,2-bis(3-aminopropoxy)ethane, m-xylylene diamine, p-xylene diamine, 2,4-diaminotoluene, 2,6-diaminotoluene, bis(4-aminocyclohexyl)methane, 3-methylheptamethylenediamine, 4,4-dimethylhepatamethylenediamine, dodecamethylenediamine, 2,2-dimethylpropylenediamine, octamethylenediamine, 3-methoxyhexamethylenediamine, 2,5-dimethylhexamethylenediamine, 2,5-dimethylheptamethylenediamine, 3-methylhepamethylenediamine, 5-methylnonamethylenediamine, 1,4-cyclohexanediamine, octadecamethylenediamine, bis(3-aminopropyl)sulfide, N-methyl-bis(3-aminopropyl)amine, hexamethylenediamine, heptamethylenediamine, 4,4′-diaminobenzophenone, nonamethylenediamine, decamethylenediamine, bis(3-aminopropyl)tetramethyldisiloxane, and bis(4-aminobutyl)tetramethyldisiloxane.

In the practice of the aforementioned reaction, substantially 2 mols of 4-hydroxyphthalic anhydride is used per 1 mol of an organic diamine. However, the amount of the organic diamine mixed with 2 mols of 4-hydroxyphthalic anhydride may be varied within the range of from 0.8 to 1.2 mols to give good results.

As the examples of usable solvent, phenolic solvent and glacial acetic acid may be mentioned. Examples of the phenolic solvents are o-cresol, p-cresol, m-cresol and mixtures thereof. When a phenolic solvent is used, it is used in a ratio such that 1 to 2 parts by weight or more thereof is added per 1 part by weight of the total weight of the reactive ingredients. Preferable reaction temperature ranges between about 100° to 140° C. In order to remove the water produced by the reaction for forming the bis(hydroxyphthalimide) from the reaction system, a non-polar solvent having a low boiling point and forming an azeotropic mixture with water, such as benzene, chlorobenzene or toluene, may be used.

The time required for the reaction is varied depending on the parameters, such as the specific kind of organic diamine used, the extent of stirring and the reaction temperature, and generally ranges from 20 minutes to 2 hours. After the completion of reaction, the reaction mixture is cooled and then the solvent is removed under a reduced pressure. Alternatively, the reaction mixture may be added to another solvent, such as methanol, to precipitate the reaction product which is then isolated by filtration.

When glacial acetic acid is used as the solvent in the aforementioned reaction, glacial acid is added in a ratio such that about 10 parts by weight thereof is present per 1 part of the total weight of all reactive ingredients. The reaction is continued for 1 to 15 hours under the reflux of glacial acetic acid. After the completion of reaction, the reaction system is cooled and the precipitate is filtered and rinsed with methanol to isolate the product bis(hydroxyphthalimide).

The bis(hydroxyphthalimide) of the invention may be polycondensed with a dicarboxylic acid dihalide to produce a polyesterimide. The thus prepared polyesterimide, included within the broad scope of this invention, is of high industrial value in that it has excellent heat resistant property and superior transparency.

Specific examples of the bis(hydroxyphthalimide) which may be used as a starting material for the production of the polyesterimides according to the invention are 1,3-bis(4-hydroxy-phthalimide)benzene and 1,4-(bis-hydroxyphthalimide)benzene.

Specific examples of the dicarboxylic acid dihalide are halogenated products of dicarboxylic acids such as terephthalic acid, isophthalic acid, phthalic acid, phenylmalonic acid, phenylsuccinic acid, benzylsuccinic acid, oxalic acid, malonic acid, succinic acid, glutaric acid, methylsuccinic acid and adipic acid. The dicarboxylic acid dihalides, which may be used conveniently in the reaction, are represented by the following general formula of:

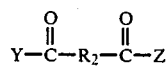

wherein $R_2$ is a difunctional organic group selected from the groups (a), (b) and (c) of:

(a) aromatic hydrocarbon groups each having 6 to 20 carbon atoms or halogenated derivatives thereof;

(b) alkylene groups; and (c) those represented by the following general formula of:

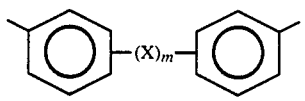

wherein X is selected from the group consisting of —O—,

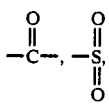

—S— and —$C_nH_{2n}$—; m is an integer of 1 or zero; and n is an integer of 1 to 5;

and wherein Y is any one of fluorine, chlorine, bromine or iodine; and Z is any one of fluorine, chlorine, bromine or iodine.

The bis(hydroxyphthalimide) may be represented by the following general formula of:

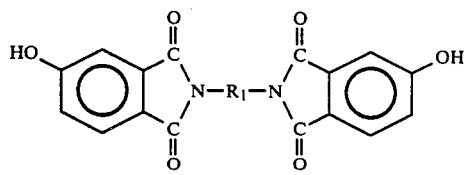

wherein $R_1$ is a difunctional organic group selected from the groups (a), (b) and (c) of:

(a) aromatic hydrocarbon groups having 6 to 20 carbon atoms or a halogenated derivative thereof;

(b) alkylene groups; and (c) those represented by the following general formula of:

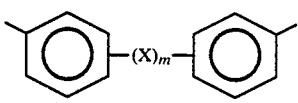

wherein X is a group selected from the group consisting of —O—,

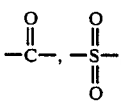

—S—, —$C_nH_{2n}$—; m is an integer of 1 or zero; and n is an integer of 1 to 5.

On the other hand, the polyesterimides obtained by the polycondensation reaction may be represented by the following formula of:

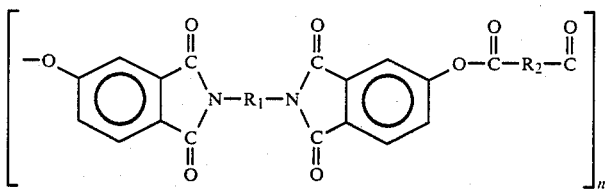

wherein $R_1$ and $R_2$ are the same as described in the general formulae representing the bis(hydroxyphthalimide) and the dicarboxylic acid dihalide.

The polycondensation reaction for preparing the polyesterimide of the invention may be effected in a polar organic solvent substantially in the absence of water. An amide system organic solvent, such as N-methyl-2-pyrrolidone, N,N-dimethylformamide or N,N-dimethylacetoamide, is used after drying the same sufficiently. A tertiary amine, such as pyridine or triethylamine, may be added to the reaction system, in order to remove hydrogen halides produced as the reaction proceeds.

The polycondensation reaction is carried out by adding substantially 1 mol of a dicarboxylic acid dihalide per 1 mol of the bis(hydroxyphthalimide). The reaction temperature ranges from 20° to 50° C., and the time required for the completion of reaction is varied depending on the specific kinds of the reactant, the reaction temperature and the extent of stirring and generally ranges from 30 minutes to 30 hours. After the completion of reaction, the reaction mixture may be added into a solvent, such as methanol, and the sedimented precipitate may be filtered to isolate the formed polyesterimide.

Other than the process wherein an organic solvent is used, an interfacial polymerization as disclosed in the "Journal of Polymer Science", vol. XL, 399 (1959) may be used. In the interfacial polymerization process, an aqueous alkali solution of bis(hydroxyphthalimide) is subjected to the interfacial polymerization with an solution of a dicarboxylic acid dihalide in an organic solvent.

FIGURE shows the relation between wavelength (nm) and transmittance (%), wherein curve 1 of polyesterimide is prepared by polycondensation from 4,4'-diaminodiphenylsulfone and bisester consisting of 4-hydroxyphthalic anhydride and terephthalic acid, curve 2 of polyimide is a commercial polyimide. polyesterimide is excellent in transparency.

The present invention will now be described more specifically with reference to some examples thereof.

EXAMPLE 1

A mixture containing 50 g of p-cresol and 30 g of toluene was added with 32.8 g (0.2 mol) of 4-hydroxyphthalic anhydride and 10.8 g (0.1 mol) of m-phenylenediamine, and heated under reflux at 120° to 125° C. for 15 minutes. Then, the azeotropic mixture composed of toluene and water produced by the reaction was distilled off for 30 minutes. The reaction mixture was allowed to stand at the room temperature to precipitate the solid product which was then filtered and rinsed with acetone. The thus separated and rinsed solid was dried in vacuum at 100° C. for 3 hours. 37.7 g of 1,3-bis(4-hydroxyphthalimide)benzene was obtained. (Yield: 94%)

The thus produced 1,3-bis(4-hydroxyphthalimide)-benzene was analysed through an infrared absorption spectrography to ascertain the absorption spectrum at 3300 cm$^{-1}$ showing the presence of the OH group and the absorption spectra at 1700 cm$^{-1}$ and at 1770 cm$^{-1}$ showing the presence of carbonyl of the imide group. Another sample of the 1,3-bis(4-hydroxyphthalimide)-benzene was subjected to the proton nuclear magnetic resonance spectrometry in a dimethylsulfoxide substituted with heavy hydrogen while using tetramethylsilane as the internal standard. The result was that the signal of hydroxyl group (broad, 2H) at 11.0 ppm and the signal of phenyl group (10H) at 7.1 to 8.0 ppm were found. The result of the elemental analysis conducted for the identification of the reaction product as $C_{22}H_{12}O_6N_2$ will be set forth below:

|  | C | H | N |
| --- | --- | --- | --- |
| Found: | 66.28% | 2.80% | 6.77% |
| Calculated: | 66.00% | 3.00% | 7.00% |

The 1,3-bis(4-hydroxyphthalimide)benzene may be refined by recrystallization or re-precipitation. The melting point of the product was confirmed that it was not lower than 360° C.

EXAMPLE 2

Glacial acetic acid was used as the solvent. A mixture containing 30 ml of glacial acetic acid, 3.28 g (0.02 mol) of 4-hydroxyphthalic acid, and 1.08 g (0.01 mol) of m-phenylenediamine was heated at 120° C. for 8 hours under reflux. After allowing to stand the reaction mixture at the room temperature, the sedimented solid was filtered and rinsed with methanol. The product was dried under vacuum at 100° C. for 3 hours. 3.88 g (Yield: 96%) of 1,3-bis(4-hydroxyphthalimide)-benzene was obtained. The melting point of the product was not lower than 360° C. The infrared spectrum of the product was similar to that of the compound produced in Example 1.

EXAMPLE 3

Similar procedures were repeated as in Example 1, except that 4-chloro-1,3-diaminobenzene was used in place of m-phenylenediamine. 1,3-bis(4-hydroxyphthalimide)-4-chlorobenzene was produced at a yield of 69%, and had a melting point of not lower than 360° C. In the infrared absorption spectrum chart, the absorption spectrum at 3300 cm$^{-1}$ showing the presence of the OH group and the absorption spectra at 1700 cm$^{-1}$ and at 1775 cm$^{-1}$ showing the presence of carbonyl of the imide group. The result of the elemental analysis conducted for the identification of the reaction product as $C_{22}H_{11}O_6N_2Cl$ will be set forth below:

|  | C | H | N |
| --- | --- | --- | --- |
| Found: | 60.47% | 2.55% | 6.57% |

|  | C | H | N |
|---|---|---|---|
| Calculated: | 60.76% | 2.53% | 6.44% |

EXAMPLE 4

Similar procedures were repeated as in Example 1, except that 4,4'-diaminodiphenylmethane was used in place of m-phenylenediamine. 4,4'-bis(4-hydroxyphthalimide)diphenylmethane was produced at a yield of 72%, and had a melting point of 317° to 319° C. In the infrared absorption spectrum chart, the absorption spectrum at 3550 cm$^{-1}$ showing the presence of the OH group and the absorption spectra at 1700 cm$^{-1}$ and at 1770 cm$^{-1}$ showing the presence of carbonyl of the imide group. The result of the elemental analysis conducted for the identification of the reaction product as $C_{29}H_{18}O_6N_2$ will be set forth below:

|  | C | H | N |
|---|---|---|---|
| Found: | 70.75% | 3.71% | 5.83% |
| Calculated: | 71.02% | 3.67% | 5.71% |

EXAMPLE 5

Similar procedures were repeated as in Example 1, except that 4,4'-diaminodiphenylsulfone was used in place of m-phenylenediamine. 4,4'-bis(4-hydroxyphthalimide)diphenylsulfone was produced at a yield of 52%, and had a melting point of 340° to 342° C. In the infrared absorption spectrum chart, the absorption spectrum at 3400 cm$^{-1}$ showing the presence of the OH group and the absorption spectra at 1710 cm$^{-1}$ and at 1775 cm$^{-1}$ showing the presence of carbonyl of the imide group. The result of the elemental analysis conducted for the identification of the reaction product as $C_{28}H_{16}O_8N_2S$ will be set forth below:

|  | C | H | N |
|---|---|---|---|
| Found: | 62.43% | 2.90% | 5.06% |
| Calculated: | 62.22% | 2.96% | 5.19% |

EXAMPLE 6

Similar procedures were repeated as in Example 1, except that 1,6-hexamethylene diamine was used in place of m-phenylenediamine. 1,6-bis(4-hydroxyphthalimide)hexane was produced at a yield of 72%, and had a melting point of 259° to 260° C. In the infrared absorption spectrum chart, the absorption spectrum at 3280 cm$^{-1}$ showing the presence of the OH group and the absorption spectra at 1680 cm$^{-1}$ and at 1765 cm$^{-1}$ showing the presence of carbonyl of the imide group. The result of the elemental analysis conducted for the identification of the reaction product as $C_{22}H_{20}O_6N_2$ will be set forth below:

|  | C | H | H |
|---|---|---|---|
| Found: | 64.44% | 5.01% | 6.99% |
| Calculated: | 64.71% | 4.90% | 6.86% |

EXAMPLE 7

Similar procedures were repeated as in Example 1, except that p-phenylenediamine was used in place of m-phenylenediamine. 1,4-bis(4-hydroxyphthalimide)benzene was produced at a yield of 78%, and had a melting point of not lower than 360° C. In the infrared absorption spectrum chart, the absorption spectrum at 3350 cm$^{-1}$ showing the presence of the OH group and the absorption spectra at 1710 cm$^{-1}$ and at 1775 cm$^{-1}$ showing the presence of carbonyl of the imide group. The result of the elemental analysis conducted for the identification of the reaction product as $C_{22}H_{12}O_6N_2$ will set forth below:

|  | C | H | N |
|---|---|---|---|
| Found: | 66.13% | 2.98% | 6.89% |
| Calculated: | 66.00% | 3.00% | 7.00% |

EXAMPLE 8

Similar procedures were repeated as in Example 1, except that 4,4'-diaminodiphenyl ether was used in place of m-phenylenediamine. 4,4'-bis(4-hydroxyphthalimide)diphenyl ether was produced at a yield of 80%, and had a melting point of 309° to 311° C. In the infrared absorption spectrum chart, the absorption spectrum at 3320 cm$^{-1}$ showing the presence of the OH group and the absorption spectra at 1695 cm$^{-1}$ and at 1770 cm$^{-1}$ showing the presence of carbonyl of the imide group. The result of the reaction product as $C_{28}H_{16}O_7N_2$ will be set forth below:

|  | C | H | N |
|---|---|---|---|
| Found: | 68.20% | 3.22% | 5.70% |
| Calculated: | 68.29% | 3.25% | 5.69% |

EXAMPLE 9

540 mg (1 millimol of 4,4'bis(4-hydroxyphthalimide)diphenylsulfone and 202 mg (1 millimol) of terephthalic acid dichloride were 10 ml of N-methyl-2-pyrrolidone which had been dehydrated and refined preliminarily. The thus prepared solution was added with 158 mg (2 millimols of pyridine and agitated at the room temperature for 15 hours in a nitrogen atmosphere. After the completion of reaction, the reaction product was added into 100 ml of methanol, whereupon a white solid was formed. The white solid was filtered and rinsed sufficiently with water, methanol and acetone, and then dried at 100° C. for 5 hours under reduced pressure. A polyesterimide represented by the following structural formula of:

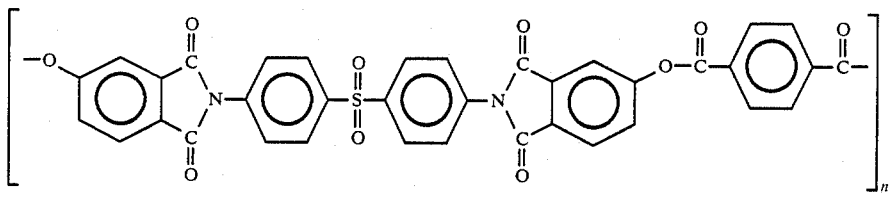

was produced at a yield of 480 mg (Yield: 72%). The thermal decomposition temperature was measured in air at a temperature raising rate of 10° C./minute, and shown by the temperature at which the weight of the specimen was reduced by 10%. The thus measured thermal decomposition temperature was 440° C. The infrared absorption spectrometry of the polyesterimide was that the absorption peaks at 1775 and 1720 cm$^{-1}$ showing the presence of carbonyl of the imide group were found and that the absorption peak at 3300 cm$^{-1}$ showing the presence of the OH group was not found. The result of the elemental analysis conducted for the identification of the reaction product as $C_{36}H_{14}O_{10}H_2S$ will be set forth below:

|  | C | H | N |
|---|---|---|---|
| Found: | 64.53% | 2.48% | 4.02% |
| Calculated: | 64.48% | 2.69% | 4.18% |

EXAMPLE 10

2.70 g (5 millimols) of 4,4'-bis(4-hydroxyphtahlimide)diphenylsulfone was dissolved in 150 ml of an aqueous solution containing 0.40 g (10 millimols) of sodium hydroxide. The solution was then added with 10 ml of an aqueous solution containing 0.29 g (1 millimol) of sodium laurate and 75 ml of a solution containing 1.01 g (5 millimols) of terephthalic acid dichloride dissolved in benzene, and the admixture was stirred vigorously at the room temperature for an hour. After the completion of reaction, the reaction product was added into 500 ml of acetone, whereupon a white solid was separated. The white solid was filtered and rinsed sufficiently with water and acetone, and then dried at 100° C. for 6 hours under reduced pressure. 2.24 g (Yield: 67%) of a polyesterimide was produced. The result of spectrometry of the thus produced polyesterimide were the same as those of the polymer produced by Example 9.

EXAMPLE 11

2.70 g (5 millimols) of 4,4'-bis(4-hydroxyphthalimide)-diphenylsulfone was dissolved in 150 ml of an aqueous solution containing 0.40 g (10 millimols) of sodium hydroxide. The solution was then added with 10 ml of an aqueous solution containing 0.29 g (1 millimol) of sodium lauryl sulfate and 75 ml of a solution containing 1.01 g (5 millimols) of isophthalic acid dichloride and dissolved in benzene, and the admixture was stirred vigorously at the room temperature for an hour. The reaction product was added into 500 ml of acetone, whereupon a white solid was separated. The white solid was filtered and rinsed sufficiently with water and acetone, and then dried at 100° C. for 5 hours under reduced pressure. A polyesterimide represented by the following structural formula of:

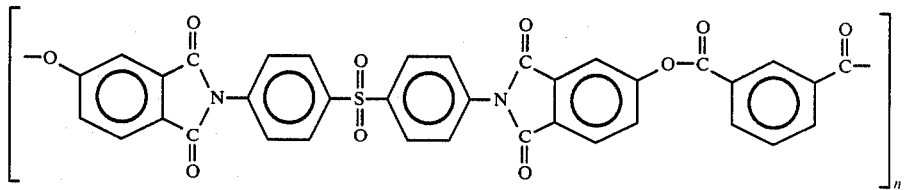

was produced at a yield of 2.01 g (Yield: 60%). The thermal decomposition temperature was 444° C. The result of infrared absorption spectrometry of the polyesterimide was that the absorption peaks at 1775 and 1720 cm$^{-1}$ showing the presence of carbonyl of the imide group were found and that the absorption peak at 3300 cm$^{-1}$ showing the presence of the OH group was not found. The result of the elemental analysis conducted for the identification of the reaction product as $C_{36}H_{14}O_{10}N_2S$ will be set forth below:

|  | C | H | N |
|---|---|---|---|
| Found: | 64.38% | 2.71% | 4.20% |
| Calculated: | 64.48% | 2.69% | 4.18% |

EXAMPLE 12

Polycondensation was carried out generally following to the procedures as described in Example 10, except that 1,4-bis(4-hydroxyphthalimide)benzene was used in place of 4,4'-bis(4-hydroxyphthalimide)diphenylsulfone. A polyesterimide represented by the following structural formula of:

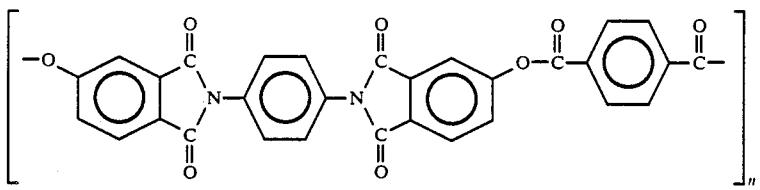

was produced at a yield of 62%. The polyesterimide had a thermal decomposition temperature of 450° C. The result of the infrared absorption spectrometry was that absorption peaks at 1720 and 1775 cm$^{-1}$ showing the presence of carbonyl of imide group were found. The result of the elemental analysis conducted for the identification of the reaction product as $C_{30}H_{14}O_8N_2$ will be set forth below:

|  | C | H | N |
|---|---|---|---|
| Found: | 67.85% | 2.68% | 5.30% |
| Calculated: | 67.92% | 2.64% | 5.28% |

|  | C | H | N |
|---|---|---|---|
| Calculated: | 67.92% | 2.64% | 6.28% |

EXAMPLE 14

Polycondensation was carried out generally following to the procedures as described in Example 10, except that 1,3-bis(4-hydroxyphthalimide)diphenyl ether was used in place of 4,4'-bis(4-hydroxyphthalimide)-diphenylsulfone. A polyesterimide represented by the following structural formula of:

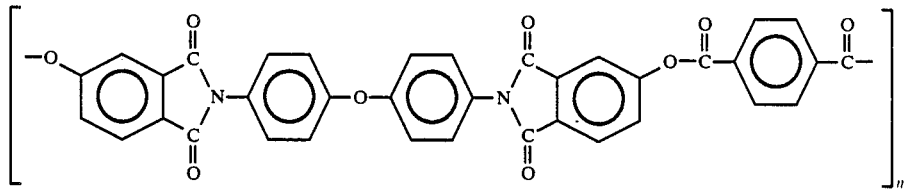

EXAMPLE 13

Polycondensation was carried out generally following to the procedures as described in Example 10, except that 1,3-bis(4-hydroxyphthalimide)benzene was used in place of 4,4'-bis(4-hydroxyphthalimide)diphenylsulfone. A polyesterimide represented by the following structural formula of:

was produced at a yield of 56%. The polyesterimide had a thermal decomposition temperature of 430° C. The result of the infrared absorption spectrometry was that absorption peaks at 1715 and 1775 cm$^{-1}$ showing the presence of carbonyl of imide group were found. The result of the elemental analysis conducted for the identification of the reaction product as $C_{36}H_{18}O_9N_2$ will be set forth below:

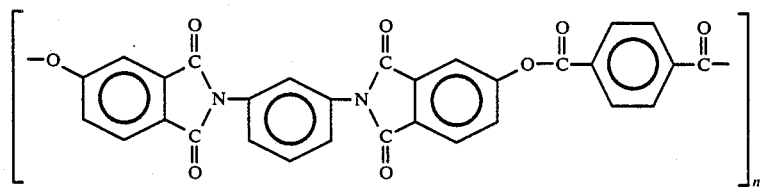

was produced at a yield of 70%. The polyesterimide had a thermal decomposition temperature of 410° C. The result of the infrared absorption spectrometry was that absorption peaks at 1710 and 1775 cm$^{-1}$ showing the presence of carbonyl of imide group were found. The result of the elemental analysis conducted for the identification of the reaction product as $C_{30}H_{14}O_8N_2$ will be set forth below:

|  | C | H | N |
|---|---|---|---|
| Found: | 68.05% | 2.68% | 5.15% |

|  | C | H | N |
|---|---|---|---|
| Found: | 69.30% | 2.68% | 4.45% |
| Calculated: | 59.45% | 2.89% | 4.50% |

EXAMPLE 15

Polycondensation was carried out generally following to the procedures as described in Example 10, except that 4,4'-bis(hydroxyphthalimide)diphenylmethane was used in place of 4,4'-bis(4-hydroxyphthalimide)-diphenylsulfone. A polyesterimide represented by the following structural formula of:

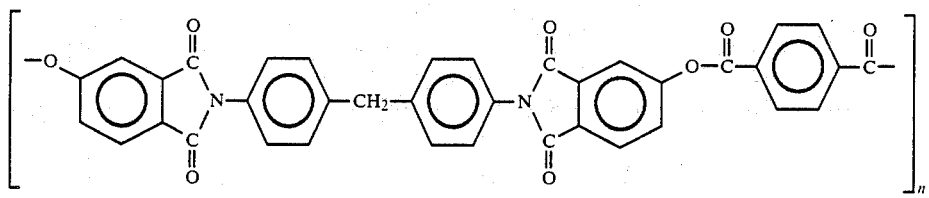

was produced at a yield of 66%. The polyesterimide had a thermal decomposition temperature of 438° C. The result of the infrared absorption spectrometry was that absorption peaks at 1715 and 1775 cm$^{-1}$ showing the presence of carbonyl of imide group were found. The result of the elemental analysis conducted for the identification of the reaction product as $C_{37}H_{18}O_8N_2$ will set forth below:

|  | C | H | N |
| --- | --- | --- | --- |
| Found: | 71.50% | 3.28% | 4.50% |
| Calculated: | 71.61% | 3.23% | 4.52% |

EXAMPLE 16

Polycondensation was carried out generally following to the procedures as described in Example 10, except that 1,6-bis(4-hydroxyphthalimide)hexane was used in place of 4,4'-bis(4-hydroxyphthalimide)diphenylsulfone. A polyesterimide represented by the following structural formula of:

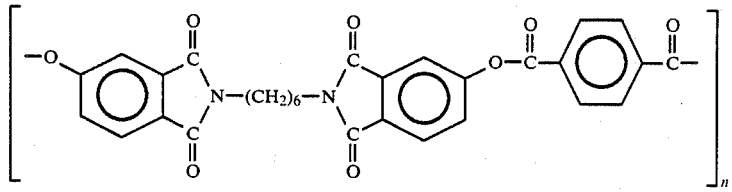

was produced at a yield of 77%. The polyesterimide had a thermal decomposition temperature of 400° C. The result of the infrared absorption spectrometry was that absorption peaks at 1700 and 1770 cm$^{-1}$ showing the presence of carbonyl of imide group were found. The result of the elemental analysis conducted for the identification of the reaction product as $C_{30}H_{24}O_8N_2$ will be set forth below:

|  | C | H | N |
| --- | --- | --- | --- |
| Found: | 66.98% | 4.01% | 5.21% |

-continued

|  | C | H | N |
| --- | --- | --- | --- |
| Calculated: | 66.91% | 4.09% | 5.20% |

EXAMPLE 17

Polycondensation was carried out generally following to the procedures as described in Example 11, except that 1,4-bis(4-hydroxyphthalimide)benzene was used in place of 4,4'-bis(4-hydroxyphtahlimide)diphenylsulfone. A polyesterimide represented by the following structural formula of:

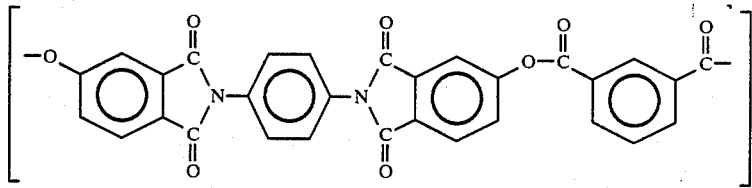

was produced at a yield of 57%. The polyesterimide had a thermal decomposition temperature of 412° C. The result of the infrared absorption spectrometry was that absorption peaks at 1715 and 1770 cm$^{-1}$ showing the presence of carbonyl of imide group were found. The result of the elemental analysis conducted for the identification of the reaction product as $C_{30}H_{14}O_8N_2$ will be set forth below:

|  | C | H | N |
| --- | --- | --- | --- |
| Found: | 67.68% | 2.68% | 5.23% |
| Calculated: | 67.92% | 2.64% | 5.28% |

EXAMPLE 18

Polycondensation was carried out generally following to the procedures as described in Example 11, except that 1,3-bis(4-hydroxyphthalimide)benzene was used in place of 4,4'-bis(4-hydroxyphthalimide)diphenylsulfone. A polyesterimide represented by the following structural formula of:

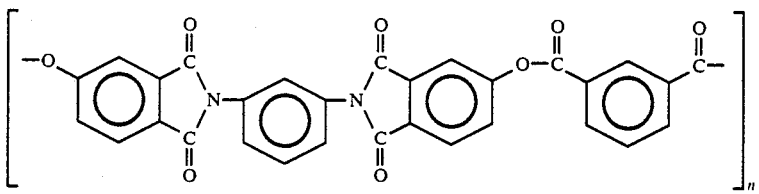

was produced at a yield of 62%. The polyesterimide had a thermal decomposition temperature of 405° C. The result of the infrared absorption spectrometry was that absorption peaks at 1710 and 1775 cm$^{-1}$ showing the presence of carbonyl of imide group were found. The result of the elemental analysis conducted for the identification of the reaction product as $C_{30}H_{14}O_8N_2$ will be set forth below:

|  | C | H | N |
|---|---|---|---|
| Found: | 67.80% | 2.69% | 5.23% |
| Calculated: | 67.92% | 2.64% | 5.28% |

EXAMPLE 19

Polycondensation was carried out generally following to the procedures as described in Example 11, except that 4,4'-bis(4-hydroxyphthalimide)diphenyl ether was used in place of 4,4'-bis(4-hydroxyphthalimide)diphenylsulfone. A polyesterimide represented by the following structural formula of:

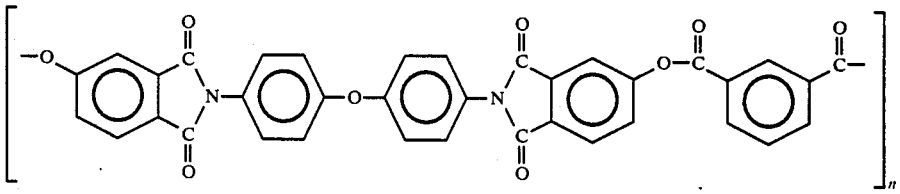

was produced at a yield of 44%. The polyesterimide had a thermal decomposition temperature of 434° C. The result of the infrared absorption spectrometry was that absorption peaks at 1715 and 1775 cm$^{-1}$ showing the presence of carbonyl of imide group were found. The result of the elemental analysis conducted for the identification of the reaction product as $C_{36}H_{18}O_{10}N_2$ will be set forth below:

|  | C | H | N |
|---|---|---|---|
| Found: | 69.38% | 2.92% | 4.48% |

| -continued | | | |
|---|---|---|---|
|  | C | H | N |
| Calculated: | 69.45% | 2.89% | 4.50% |

EXAMPLE 20

Polycondensation was carried out generally following to the procedures as described in Example 11, except that 4,4'-bis(4-hydroxyphthalimide)diphenylmethane was used in place of 4,4'-bis(4-hydroxyphthalimide)diphenylsulfone. A polyesterimide represented by the following structural formula of:

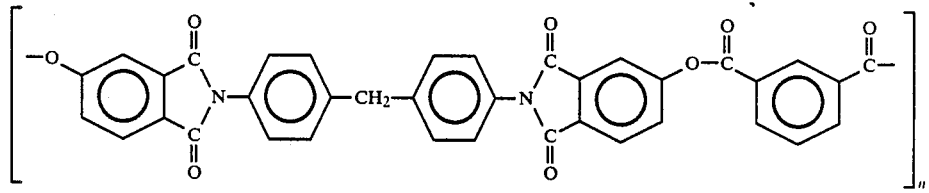

was produced at a yield of 59%. The polyesterimide had a thermal decomposition temperature of 442° C. The result of the infrared absorption spectrometry was that absorption peaks at 1715 and 1770 cm$^{-1}$ showing the presence of carbonyl of imide group were found. The result of the elemental analysis conducted for the identification of the reaction product as $C_{37}H_{28}O_8N_2$ will be set forth below:

|  | C | H | N |
|---|---|---|---|
| Found: | 71.50% | 3.20% | 4.58% |
| Calculated: | 71.61% | 3.23% | 4.52% |

EXAMPLE 21

Polycondensation was carried out generally following to the procedures as described in Example 11, except that 1,6'-bis(4-hydroxyphthalimide)hexane was used in place of 4,4'-bis(4-hydroxyphthalimide)diphenylsulfone. A polyesterimide represented by the following structural formula of:

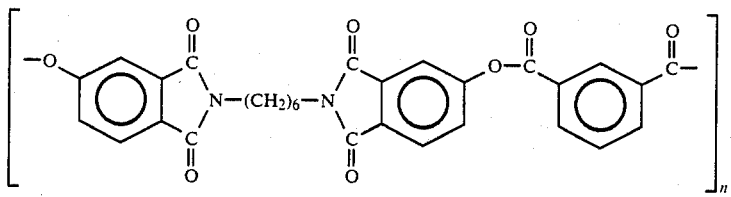

was produced at a yield of 67%. The polyesterimide had a thermal decomposition temperature of 405° C. The result of the infrared absorption spectrometry was that absorption peaks at 1700 and 1770 cm$^{-1}$ showing the presence of carbonyl of imide group were found. The result of the elemental analysis conducted for the identification of the reaction product as $C_{30}H_{22}O_8N_2$ will be set forth below:

|  | C | H | N |
|---|---|---|---|
| Found: | 66.80% | 4.06% | 5.13% |
| Calculated: | 66.91% | 4.09% | 5.20% |

As has been described in detail hereinabove, the bis(hydroxyphthalimide) provided by the present invention has two intramolecular imide rings and active hydroxide groups, and may be conveniently used as a starting monomer for the production of a polymer having imide rings, such as polyimides, polyesterimides and polyamideimides. According another important aspect of the invention, a variety of polyesterimides may be produced by polycondensating the bis(hydroxyphthalimide) of the invention with various dihalogenated dicarboxylic acids to produce polymers which are superior in heat resistant property and excellent in transparency.

What is claimed is:

1. A bis(hydroxyphthalimide) represented by the following formula:

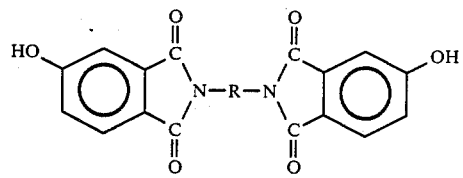

wherein R is a difunctional organic group selected from the groups (a), (b) and (c) wherein:
 (a) is an aromatic hydrocarbon group selected from the group consisting of m-phenylene, p-phenylene and chloro m-phenylene;
 (b) is hexylene; and
 (c) is diphenylmethane, diphenylsulfide, diphenylsulfone, diphenylether or diphenylketone.

2. The bis(hydroxyphthalimide) according to claim 1, wherein R is m-phenylene, p-phenylene or chloro m-phenylene.

3. The bis(hydroxyphthalimide) according to claim 1, wherein R is hexylene ($-C_6H_{12}-$).

4. The bis(hydroxyphthalimide) according to claim 1, wherein R is diphenylmethane, diphenylsulfide, diphenylsulfone, diphenyl ether or diphenyl ketone.

* * * * *